United States Patent [19]

Ueshima et al.

[11] 4,419,270
[45] Dec. 6, 1983

[54] OXIDATION CATALYST

[75] Inventors: Michio Ueshima, Nishinomiya; Yoshiyuki Takahashi, Suita; Ritsuo Kitada, Takatsuki; Isao Nagai, Suita, all of Japan

[73] Assignee: Nippon Shokubai Kagaku Kogyo Co. Ltd., Osaka, Japan

[21] Appl. No.: 275,243

[22] Filed: Jun. 19, 1981

[30] Foreign Application Priority Data

Jun. 26, 1980 [JP] Japan .................................. 55-85919
Apr. 16, 1981 [JP] Japan .................................. 56-56238
Apr. 17, 1981 [JP] Japan .................................. 56-56906
Apr. 22, 1981 [JP] Japan .................................. 56-59782
Apr. 24, 1981 [JP] Japan .................................. 56-61405

[51] Int. Cl.³ ...................... B01J 23/22; B01J 23/28; B01J 27/18
[52] U.S. Cl. ...................................... 502/209; 502/208
[58] Field of Search ................................ 252/435, 437

[56] References Cited

U.S. PATENT DOCUMENTS 4,225,466  9/1980  Wada et al. ................... 252/437 X
4,256,914  3/1981  Umemura et al. ............. 252/437 X
4,273,676  6/1981  Matsumoto et al. .......... 252/437 X Primary Examiner—W. J. Shine
Attorney, Agent, or Firm—Sherman & Shalloway

[57] ABSTRACT

A catalyst for the vapor-phase oxidation of an unsaturated hydrocarbon, alcohol, saturated aliphatic aldehyde or unsaturated aliphatic aldehyde having 4 carbon atoms, said catalyst comprising a molybdovanadophosphoric acid having X-ray diffraction lines (Cu-K$_\alpha$ radiation) at $2\theta =$ about 26.2°, about 10.5°, about 21.3° and about 30.3° and a crystal structure approximating that of its salt, and said catalyst having the composition represented by the general formula $$P_a Mo_b V_c X_d Y_e O_f$$

wherein the dissociable protons of the molybdovanadophosphoric acid are omitted, X represents at least one element selected from the group consisting of sodium, potassium, rubidium, cesium, thallium, beryllium, magnesium, calcium, strontium, and barium, Y represents at least one element selected from the group consisting of copper, silver, arsenic, antimony, tellurium, cobalt, bismuth and zirconium, and the subscripts a to f represent the atomic proportions of the respective elements, provided that when b is 12, a is 0.1–3.0,
c is 0–6.0 (exclusive of 0),
d is 0–10.0,
e is 0–5.0, and
f is a value determined by the atomic valences and atomic proportions of the respective elements.

2 Claims, No Drawings

OXIDATION CATALYST

This invention relates to an oxidation catalyst and a process for preparation thereof. More specifically, it pertains to a molybdovanadophosphoric acid catalyst for the catalytic vapor-phase oxidation of an unsaturated hydrocarbon having 4 carbon atoms such as isobutylene, an alcohol having 4 carbon atoms such as tertiary butanol, a saturated aliphatic aldehyde having 4 carbon atoms such as isobutyraldehyde, or an unsaturated aliphatic aldehyde having 4 carbon atoms such as methacrolein to produce the corresponding oxidation product such as methacrylic acid, and to a process for preparing the aforesaid catalyst.

Heteropolyacids have attracted attention as solid acid oxidation catalysts because of their strong acidity and high oxidizing power, and extensive technical development has been achieved in recent years for their application. In particular, a molybdovanadophosphoric acid has a strong oxidizing ability. It easily oxidizes other compounds and is itself reduced. The reduced molybdovanadophosphoric acid, however, can be easily re-oxidized in the presence of a suitable oxygen source. Accordingly, its ability as a vapor-phase oxidation catalyst is highly evaluated, and extensive research and development work has been undertaken in order to use it efficiently in this field. Specifically, molybdovanadophosphoric acid is frequently used in the production of methacrylic acid from isobutylene, tertiary butanol or isobutyraldehyde as a starting material. In particular, molybdovanadophosphoric acid has been extensively investigated for use in the field of producing methacrylic acid from isobutylene or tertiary butanol.

Many two-step processes have been proposed for the production of methacrylic acid by the vapor-phase oxidation of isobutylene or tertiary butanol. Such processes generally comprise a first step of oxidizing isobutylene or tertiary butanol in the vapor phase on a catalyst to form methacrolein and a second step of further oxidizing methacrolein on a catalyst in the vapor phase to form methacrylic acid. Various proposals have been made for the use of molybdovanadophosphoric acid, a kind of heteropolyacid, in the second step. Although molybdovanadophosphoric acid is characterized by having strong oxidizing activity in vapor-phase oxidation, it has the defect that a consecutive reaction of oxidizing the resulting desired product tends to take place and the desired product is difficult to obtain with good selectivity in good yields. Furthermore, from the standpoint of producing practical catalysts, molybdovanadophosphoric acid has generally very poor moldability and mechanical strength. When various manufacturing methods for increasing its strength are employed, the catalyst generally gives decreased yields. Thus, it is difficult to obtain a catalyst having high strength for industrial application and being capable of affording satisfactory yields. Many investigations have been made in recent years in regard to molybdovanadophosphoric acid, but no molybdovanadophosphoric acid catalyst satisfactory for industrial application has been discovered.

Vapor-phase oxidation of methacrolein by using a composition consisting of a major proportion of molybdovanadophosphoric acid or both phosphorus and molybdenum, and other elements as a catalyst has been reported, for example, in Japanese Laid-Open Patent Publications Nos. 15817/1973, 95921/1974, 126616/1974, 82013/1975, 62220/1977, 122317/1977 and 31615/1978, and Japanese Patent Publications Nos. 23013/1975, 31327/1977 and 14052/1978. The catalysts disclosed in these patent documents, however, have not proved to be satisfactory for industrial application because the yield of the desired methacrylic acid is low.

The present inventors, in the course of their investigations about the structure of the molybdovanadophosphoric acid and its activity and selectivity for the formation of methacrylic acid and its strength, performed the vapor-phase oxidation of methacrolein in the presence of, as a catalyst, a molybdovanadophosphoric acid composed of phosphorus, molybdenum, vanadium and oxygen and having a crystal structure approximating that of its salt, the catalyst being prepared in the presence of a nitrogen-containing heterocyclic compound. This led to the discovery that the catalyst exhibits good selectivity for methacrylic acid and a good methacrylic acid yield and moreover has very much improved strength; that an improved catalyst can be obtained by adding an alkali metal (e.g., sodium, potassium, rubidium or cesium), an alkaline earth metal (e.g., beryllium, magnesium, calcium, strontium or barium), or thallium to the above molybdovanadophosphoric acid; and that a molybdovanadophosphoric acid obtained by further adding other elements, especially copper, silver, arsenic, antimony, tellurium, cobalt, bismuth or zirconium, exhibits a very high level of selectivity and yield and scarcely changes with time in a continuous reaction.

According to this invention, there is provided a catalyst for the vapor-phase oxidation of an unsaturated hydrocarbon, alcohol, saturated aliphatic aldehyde or unsaturated aliphatic aldehyde having 4 carbon atoms, said catalyst comprising a molybdovanadophosphoric acid having X-ray diffraction lines (Cu-K$_\alpha$ radiation) at $2\theta$=about 26.2°, about 10.5°, about 21.3° and about 30.3° and a crystal structure approximating that of its salt, and said catalyst having the composition represented by the general formula $$P_a Mo_b V_c X_d Y_e O_f$$

wherein the dissociable protons of the molybdovanadophosphoric acid are omitted, X represents at least one element selected from the group consisting of sodium, potassium, rubidium, cesium, thallium, beryllium, magnesium, calcium, strontium and barium, Y represents at least one element selected from the group consisting of copper, silver, arsenic, antimony, tellurium, cobalt, bismuth and zirconium, and the subscripts a to f represent the atomic proportions of the respective elements, provided that when b is 12, a is 0.1–3.0, preferably 0.1–2.0, more preferably 0.5–2.0, c is 0–6.0 (exclusive of 0), preferably 0.1–4.0, more preferably 0.1–2.5, d is 0–10.0, preferably 0–5.0, more preferably 0.05–3.5, e is 0–5.0, preferably 0.05–3.0, and f is a value determined by the atomic valences and atomic proportions of the respective elements.

The present invention is described in more detail below.

The nitrogen-containing heterocyclic compound used to prepare the molybdovanadophosphoric acid having a crystal structure approximating that of its salt includes compounds which can form salts with heteropolyacids and can be split off. Especially preferred nitrogen-containing heterocyclic compounds are pyridine, piperidine, piperazine, pyrimidine and the derivatives of these. The use of inorganic salts of these compounds, such as their nitrates, sulfates or hydrochlorides is recommended because it can prevent occurrence of offensive odors during catalyst preparation and these compounds can be recovered for re-use. Five-membered cyclic compounds such as pyrrolidine, pyrroline, pyrazole and pyrazoline and six-membered cyclic compounds such as pyridazine and pyrazine can also be used as the nitrogen-containing heterocyclic compounds in this invention.

Compounds other than the above-specified nitrogen compounds, for example aliphatic amines such as methylamine, ethylamine, triethylamine, and ethanolamines or polyamines such as hydrazine and ethylenediamine, may undergo decomposition by the heteropolyacids during catalyst preparation and do not lead to the desired free molybdovanadophosphoric acid having a crystal structure approximating that of its salt. The resulting catalyst does not have superior activity and selectivity.

Various substances can be used as raw materials for catalyst preparation. Molybdenum compounds include, for example, molybdenum trioxide, molybdic acid, sodium molybdate, ammonium paramolybdate and phosphomolybdic acid. Examples of vanadium compounds are vanadium pentoxide, sodium metavanadate, ammonium metavanadate, vanadyl oxalate and vanadyl sulfate. Phosphorus compounds include, for example, phosphoric acid, disodium hydrogen phosphate, ammonium dihydrogen phosphate and diammonium hydrogen phosphate. As the components X and Y there may be used the hydroxides, oxides, nitrates, sulfates, carbonates, halides and oxy acids of the respective elements. Metals may be used as the component Y.

The action of the nitrogen-containing heterocyclic compound in the preparation of molybdovanadophosphoric acid having a crystal structure approximating that of its salt is described with regard to pyridine taken up as an example. Molybdovanadophosphoric acid having the composition of P:Mo:V=1:11:1 (atomic ratio) prepared by a known method is a water-soluble compound. X-ray diffraction (Cu-K$_\alpha$ radiation) analysis shows that its diffraction lines appear mainly at $2\theta-8.9°$, 26.8° and 27.1°, and particularly, the intensity of the diffraction line at $2\theta=$ less than 10° is very high. On dissolving in water, molybdovanadophosphoric acid forms a reddish brown solution. When pyridine is added to this solution, orange yellow crystals form. After adding pyridine until the aqueous layer becomes colorless and clear, the crystals are collected. On treatment in a nitrogen stream at 200° to 600° C., the color of the crystals changes to deep blue indicative of reduction. When they are again treated in the air at high temperatures of 100° to 400° C., yellowish green crystals result. The infrared absorption spectrum of the resulting crystals does not contain an absorption assigned to pyridine and pyridinium and showed only a characteristic absorption of molybdovanadophosphoric acid. X-ray diffraction analysis shows that diffraction lines appear at $2\theta=$ about 26.2°, about 10.5°, about 21.3° and about 30.3°, and the intensity of the diffraction line in the vicinity of 26.2° is very high. The diffraction pattern of the crystals differs from that of free molybdovanadophosphoric acid as a starting substance, and is very similar to that of an alkali metal or ammonium salt of molybdovanadophosphoric acid. When the crystals are dissolved in water and the aqueous solution is evaporated to dryness, the X-ray diffraction of the resulting product shows that diffraction lines appear at $2\theta=$ about 8.9°, about 26.8° and about 27.1°. The diffraction pattern of this product is very similar to that of free molybdovanadophosphoric acid as a starting material.

The above fact suggests that pyridine has an action of changing the crystal structure of free molybdovanadophosphoric acid to a structure very close to the crystal structure of an alkali metal or ammonium salt of the molybdovanadophosphoric acid. The other nitrogen-containing heterocyclic compounds have also been found to have the same action as pyridine.

The process for preparing the catalyst in accordance with this invention is described below with regard to the case of using pyridine as the nitrogen-containing heterocyclic compound.

Molybdovanadophosphoric acid obtained by a known method is dissolved in water, and pyridine is added to give water-insoluble crystals. Alternatively, water-soluble compounds of molybdenum, vanadium and phosphorus respectively are dissolved in an aqueous solution containing pyridine, and the solution is acidified to give water-insoluble crystals. The X-ray diffraction analysis and infrared absorption spectrum of the crystals suggest that the resulting crystals are a pyridinium salt of molybdovanadophosphoric acid formed by the combination of the dissociable protons of molybdovanadophosphoric acid with the nitrogen atom of pyridine.

It has been found that 3 to 5 moles or more of pyridine is consumed per mole of molybdovanadophosphoric acid in the formation of these crystals. This shows that pyridine is partly adsorbed onto molybdovanadophosphoric acid. In other words, it has been found to be preferable that the amount of pyridine consumed is 3 to 5 moles or more per mole of molybdovanadophosphoric acid. Furthermore, these crystals have a much larger particle diameter than an alkali metal or ammonium salt of a heteropolyacid of this kind which is obtained by a known method. While the heteropolyacid salt of this kind is in suspended form and is difficult to filter, the crystals obtained in accordance with this invention can be easily filtered, and this brings about a great advantage in catalyst preparation.

The insoluble crystals mentioned above are molded and then dried at high temperatures in order to remove volatile matter (first group; see Examples 1 to 4 given hereinbelow). Or a compound of at least one element selected from components X and components Y is added to the resulting crystals, and the mixture is molded and dried in the same way as in the first group (second group; see Examples 5 to 21 given hereinbelow). A compound of component X is added to the water-insoluble crystals, and simultaneously, a compound of component Y is added. The mixture is molded and dried in the same way as in the first group (third group; see Examples 22 to 41). The temperature at which the catalyst precursors are dried in these first to third groups differs depending upon the properties of volatile components, and is in the range of 100° to 300° C. The dried product is heated at a temperature of 200° to 600° C. under atmospheric or reduced pressure in an atmosphere of an inert gas (e.g., nitrogen, helium, argon, or carbon dioxide gas), a reducing gas (e.g., methane, ethane, propane, ethylene or propylene), or carbon monoxide to eliminate pyridine completely, and then activated in a stream of air at a temperature of 100° to 400° C. Alternatively, the dried product may be heated in a stream of air to 350°–400° C. from room temperature to obtain a final catalyst. The catalysts obtained as above will be referred to hereinbelow as catalysts of the first, second and third groups, respectively.

With the catalyst of the first group, the surface area of the catalyst can be freely changed by selecting the type and amount of the nitrogen-containing heterocyclic compound. It has been found that, for example, when the amount of pyridine is changed between 0 and 10 moles, the specific surface area of the finished catalyst changes between 2 to 7 m$^2$/g almost proportionally to the amount of pyridine. The catalyst of the first group is composed of free molybddovanadophosphoric acid alone which has a crystal structure approximating that of its salt as stated hereinabove.

When component X is added, the catalyst of the second group is considered to be a coexisting mass of free molybdovanadophosphoric acid having a crystal structure approximating that of its salt and a component X metal salt of molybdovanadophosphoric acid. When the component X element is an alkali metal such as sodium, potassium, rubidium or cesium, both show almost the same X-ray diffraction pattern, and it is difficult to determine the product clearly to be a coexisting mass. It is, however, considered to be a coexisting mass in an atomic ratio composition because scarcely any usual X-ray diffraction lines of free molybdovanadophosphoric acid appear.

However, when the component X element is an alkaline earth element such as beryllium, magnesium, calcium, strontium or barium, the product is evidently a coexisting mass of the two, as can be seen from the results of X-ray diffraction analysis. The diffraction lines inherent to free molybdovanadophosphoric acid having a crystal structure approximating that of its salt are noted when $2\theta$ is 26.0°–26.2°, 10.4°–10.5°, 21.2°–21.3° and 30.0°–30.3°, and the diffraction lines at $2\theta = 26.0°–26.2°$ have a very high intensity. These diffraction lines quite differ from those obtained in the absence of pyridine. When a product obtained by dispersing this catalyst in water, drying it and then calcining it is subjected to X-ray diffraction analysis, a very intense diffraction line appears at $2\theta = 8.9°$. Its diffraction pattern is very close to the diffraction pattern of a partial alkaline earth salt substitution product of molybdovanadophosphoric acid obtained in the absence of pyridine. This is due presumably to the fact that the crystal structure of free molybdovanadophosphoric acid having a crystal structure approximating to that of its salt in the catalyst formed by the action of pyridine was destroyed in the presence of water. It has been found that when component Y is used instead of component X, the catalyst has a structure substantially close to the catalyst of the first group.

The structure of the catalyst of the third group differs depending upon the type of the component Y element added. From its atomic ratio, it is seen that the catalyst of the third group is mainly a coexisting mass of free molybdovanadophosphoric acid having a crystal structure approximating that of its salt and a component X metal salt of molybdovanadophosphoric acid as in the case of the catalyst of the second group. This is presumed from the occurrence of the same phenomena as in the catalyst of the second group in X-ray diffraction analysis.

In the production of methacrylic acid by vapor-phase oxidation of methacrolein, the catalysts of this invention exhibit better selectivities and yields and a longer active lifetime than those catalyst which are obtained without using pyridine. Moreover, the use of the nitrogen-containing heterocyclic compound improves the moldability and mechanical strength of the catalyst, and the reproducibility of catalyst preparation is very good.

When the nitrogen-containing heterocyclic compound is not used in the preparation of the catalyst according to this invention, filtration and molding of crystals during catalyst preparation are difficult. If the crystals are tableted, both the mechanical strength and the resistance to powderization of the molded product are very poor. When tableting is carried out in the presence of a molding aid, the strength and the resistance to powderization will be improved slightly, but the performance of the catalyst is reduced greatly and it cannot be used in practical applications. This fact also substantiate the great effect of the nitrogen-containing heterocyclic compound.

These effects exhibited by the present invention are presumably brought about synergistically by the changing of the crystal structure of molybdovanadophosphoric acid and the surface structure of the catalyst caused by the nitrogen-containing heterocyclic compound and the introduction of the component X and/or component Y.

These catalysts have good moldability and high mechanical strength as well as good performance. Hence, they can be used without a carrier. But if the heat-removing effect in a catalyst layer in an oxidation reaction is considered, carriers may also be used. Generally, inert carriers such as silica, alumina, celite, and silicon carbide are preferred, but other carriers may also be used. Furthermore, the performance of the catalyst in accordance with this invention can be upgraded by preparing it in the presence of an ammonium salt such as ammonium nitrate, ammonium chloride or ammonium sulfate.

The time of addition of the nitrogen-containing heterocyclic compound in the catalyst preparation in accordance with this invention may be those exemplified hereinabove, and may also be after the addition of the compound of X and/or Y element to molybdovanadophosphoric acid, or during the mixing of all raw materials in aqueous solution. The amount of the nitrogen-containing heterocyclic compound may be up to 20 moles, preferably 1 to 10 moles, per mole of molybdovanadophosphoric acid although differing depending upon the number of nitrogen atoms in the molecules of the nitrogen-containing heterocyclic compound.

The catalysts of this invention are used, for example, in the vapor-phase oxidation of hydrocarbons such as isobutylene and alcohols such as tertiary butanol, aldehydes such as methacrolein and isobutyraldehyde, and reaction gases containing an aldehyde such as methacrolein obtained by oxidizing a hydrocarbon, an alcohol, etc. Air is advantageous as an oxygen source in industrial practice. As diluents, there can be used inert gases such as nitrogen, carbon dioxide, helium or argon, carbon monoxide, and steam. The use of steam is advantageous in order to inhibit formation of by-products and increase the yield of the desired product.

The preferred concentration of the starting material in an oxidation reaction mixture is 0.5 to 10% by volume. The volume ratio of oxygen to the starting material is from 0.5 to 10, preferably from 1 to 5. The suitable space velocity of the starting gas is 100 to 5,000 hr$^{-1}$, preferably 500 to 2,000 hr$^{-1}$. The reaction temperature, which may be varied depending upon the starting material used, is in the range of about 220° to 350° C.

In using the catalysts of this invention, a reactor of a fixed bed type is generally used. There can also be used reactors of a fluidized bed type or a moving bed type.

The following examples specifically illustrate the preparation of the catalysts of this invention and reactions performed in the presence of such catalysts.

The conversion, selectivity and one-pass yield in these examples are defined as follows:

$$\text{Conversion (\%)} = \frac{\text{Moles of aldehyde consumed}}{\text{Moles of aldehyde fed}} \times 100$$

$$\text{Selectivity (\%)} = \frac{\text{Moles of fatty acid formed}}{\text{Moles of aldehyde consumed}} \times 100$$

$$\text{One-pass yield (\%)} = \frac{\text{Moles of fatty acid formed}}{\text{Moles of aldehyde fed}} \times 100$$

EXAMPLE 1

Disodium hydrogen phosphate (21.3 g) was dissolved in 300 ml of water. Separately, 18.3 g of sodium metavanadate was dissolved in 300 ml of hot water. The two solutions were mixed, and cooled, followed by addition of 15 ml of conc. sulfuric acid. A solution of 399 g of sodium molybdate in 600 ml of water was added to the resulting solution, and with vigorous stirring, 255 ml of conc. sulfuric acid was added gradually, followed by cooling. Then, 1200 ml of ethyl ether was added, and the mixture was vigorously shaken, and allowed to stand. The heteropolyetherate layer was withdrawn from an middle layer of the liquid and air-dried. The resulting solid was recrystallized from water and dried at 250° C. to give orange crystals. X-ray diffraction analysis, fluorescent X-ray analysis and infrared absorption spectroscopy led to the determination that the crystals obtained were free molybdovanadophosphoric acid having the composition P:Mo:V=1.09: 12:1.09 (atomic ratio excepting oxygen).

Sixty grams of the molybdovanadophosphoric acid crystals were dissolved in 200 ml of water, and 18 g of pyridine was added to give a water-insoluble precipitate. The precipitate was collected by filtration, washed with water, and then molded into cylindrical pellets having a diameter of 5 mm and a height of 5 mm. The molded product was dried at 150° C., calcined in a stream of nitrogen at 430° C. for 3 hours, and subsequently calcined in a stream of air at 350° C. for 3 hours to give a catalytic oxide having the composition P:Mo:V=1.09:12:1.09 (atomic ratio excepting oxygen) (this method of preparation will be referred to hereinbelow as method A). The above precipitate had good moldability, and the catalyst had a compression strength of more than 3.0 kg/pellet showing sufficient mechanical strength, and a specific surface area, measured by the BET method, of 6.00 m$^2$/g.

The infrared absorption spectrum of this catalyst had no characteristic absorption of pyridine and a pyridinium ion, but contained only an absorption inherent to molybdovanadophosphoric acid. The catalyst was water-soluble, and showed the properties inherent to free molybdovanadophosphoric acid. X-ray diffraction analysis showed that diffraction lines (Cu-Kα radiation) appeared at 2θ=26.2°, 10.5°, 21.3°, 30.3°, etc., and its X-ray diffraction pattern differed totally from the X-ray diffraction pattern of free molybdovanadophosphoric acid and was close to that of an alkali metal molybdovanadophosphate.

The catalyst was dissolved in water. The aqueous solution was evaporated to dryness and the residue was calcined at 250° C. The X-ray diffraction analysis of the resulting product showed that main diffraction lines (Cu-Kα radiation) appeared at 2θ=8.90°, 26.8°, 27.1°, and 20.1°, and its X-ray diffraction pattern was very close to that of free molybdovanadophosphoric acid. This shows that pyridine has an action of changing the crystal structure of molybdovanadophosphoric acid.

The resulting catalyst (50 ml) was packed into a stainless steel U-shaped tube having an inside diameter of 25 mm, and the tube was dipped in a molten salt bath at 290° C. A gaseous mixture of methacrolein, oxygen, nitrogen and water in a ratio of 1:5:34:10 was passed through the U-shaped tube at a space velocity of 1000 hr$^{-1}$. The results are shown in Table 1.

Comparative Example 1

Free molybdovanadophosphoric acid crystals having the composition P:Mo:V=1.09:12:1.09 (atomic ratio excepting oxygen) obtained in Example 1 by airdrying the heteropolyetherate were pulverized, tabletted into cylindrical pellets having a diameter of 5 mm and a height of 5 mm, and then calcined in a stream of air at 350° C. for 3 hours. The catalyst was hydroscopic and had low mechanical strength and poor moldability. The catalyst had a BET specific surface area of 2.12 m$^2$/g.

The same reaction as in Example 1 was carried out using this catalyst. The results are shown in Table 2.

EXAMPLE 2

A catalytic oxide having the composition P:Mo:V=1.09:12:1.09 (atomic ratio excepting oxygen) was prepared in the same way as in Example 1 (method A) except that piperidine was used instead of pyridine. The same reaction as in Example 1 was carried out in the presence of this catalyst except that the reaction temperature was changed to 280° C. The results are shown in Table 1.

EXAMPLE 3

A catalytic oxide having the composition P:Mo:V=1.09:12:1.09 (atomic ratio excepting oxygen) was produced in the same way as in Example 1 (method A) except that 12 g of piperazine hexahydrate was used instead of pyridine. The same reaction as in Example 1 was carried out using this catalyst except that the reaction temperature was changed to 300° C.

EXAMPLE 4

Ammonium paramolybdate (88.3 g) and 5.3 g of ammonium metavanadate were dissolved in 200 ml of heated water, and the solution was stirred. To the solution were added 20.3 g of pyridine and 5.24 g of phosphoric acid (85% by weight). Then, 40 ml of nitric acid (specific gravity 1.38; the nitric acids used in the subsequent examples had the same specific gravity) was added. With stirring, the mixture was concentrated by heating. The resulting clay-like material was molded into cylindrical pellets having a diameter of 5 mm and a height of 5 mm, dried at 250° C. for 15 hours, calcined in a stream of air at 450° C. for 4 hours, and then calcined in a stream of air at 350° C. for 3 hours to give a catalytic oxide having the composition P:Mo:V=1.09:12:1.09 (atomic ratio excepting oxygen) (this method of preparation will be referred to hereinbelow as method B).

The infrared absorption spectrum of this catalyst showed only a characteristic absorption of molybdovanadophosphoric acid, and contained no characteristic absorption assigned to pyridine and a pyridinium ion. This catalyst was well soluble in water, and showed the properties inherent to free molybdovanadophosphoric acid. When it was subjected to X-ray diffraction analysis, its X-ray diffraction pattern was close to that of an alkali metal molybdovanadophosphate.

The same reaction as in Example 1 was carried out using the resulting catalyst except that the reaction temperature was changed to 300° C. The results are shown in Table 1.

Comparative Example 2

A catalytic oxide having the composition P:Mo:V=1.09:12:1.09 (atomic ratio excepting oxygen) was prepared (method B) in the same way as in Example 4 except that the pyridine was not used. The same reaction as in Example 1 was carried out using the resulting catalyst except that the reaction temperature was changed to 300° C. The results are shown in Table 2.

EXAMPLE 5

Molybdenum trioxide (144.0 g), 8.27 g of vanadium pentoxide, and 12.5 g of phosphoric acid (85% by weight) were added to 1 liter of water, and the mixture was heated under reflux for 24 hours. The resulting reddish brown solution was filtered to remove the insoluble solid. The solid was concentrated to form reddish brown crystals. X-ray diffraction analysis, fluorescent X-ray analysis and infrared absorption spectroscopy showed that these crystals were molybdovanadophosphoric acid having the composition P:Mo:V=1.09:12:1.09 (atomic ratio excepting oxygen). The crystals were dried, and 81.0 g of the dried product was dissolved in 200 ml of water. A solution of 20 g of pyridine and 0.81 g of cesium nitrate in 50 ml of water was added, and with stirring, the solution was concentrated by heating. The resulting orange yellow clay-like material was molded into cylindrical pellets having a diameter of 5 mm and a height of 5 mm, dried at 150° C., calcined in a stream of air at 430° C. for 3 hours, and calcined in a stream of air at 400° C. for 3 hours to give a catalytic oxide having the composition P:Mo:V:Cs=1.09:12:1.09:0.1 (atomic ratio excepting oxygen) (this method of preparation is referred to hereinbelow as method C).

X-ray diffraction analysis showed that main diffraction lines were noted when $2\theta$ was 26.2°, 10.5°, 21.3°, 30.3° and 18.4°. It was thus recognized that the catalyst consisted of a major proportion of molybdovanadophosphoric acid having a crystal structure approximating that of its salt and a minor proportion of a cesium salt thereof. The catalyst showed good moldability and had a compression strength of more than 3.0 kg/pellet.

The same reaction as in Example 1 was carried out continuously except that the reaction temperature was changed to 260° C. The results of the reaction after the lapse of 100 hours and 1000 hours respectively are shown in Table 3.

Comparative Example 3

A catalytic oxide having the composition P:Mo:V:Cs=1.09:12:1.09:0.1 (atomic ratio excepting oxygen) was prepared in the same way as in Example 5 except that pyridine was not used, and the step of removing pyridine by calcination at 430° C. for 3 hours was omitted.

X-ray diffraction analysis showed that main diffraction lines appeared at $2\theta=8.9°$, 26.1°, 10.5°, 30.3° and 18.4°, and the diffraction line assigned to free molybdovanadophosphoric acid ($2\eta=8.9°$) had a relatively high intensity. The catalyst showed good moldability and had a compression strength of less than 0.5 kg/pellet.

The same reaction as in Example 5 was carried out using the resulting catalyst, but the results are shown in Table 4.

EXAMPLE 6

A catalytic oxide having the composition P:Mo:V:Sr=1.09:12:1.09:0.1 (atomic ratio excepting oxygen) was prepared in the same way as in Example 5 (method C) except that 0.88 g of strontium nitrate was used instead of cesium nitrate.

The X-ray diffraction analysis of the resulting catalyst showed that main diffraction lines appeared at $2\theta=26.1°$, 10.5°, 21.3° and 30.3°, and its X-ray diffraction pattern was quite different from the X-ray diffraction pattern ($2\theta=8.9°$, 19.7°, 26.7° and 29.0°) of a partial strontium substitution product of molybdovanadophosphoric acid.

A part of the catalyst was dispersed in water, and the aqueous dispersion was evaporated to dryness, and the residue was calcined. The X-ray diffraction of the product showed that main diffraction lines appeared at $2\theta=8.9°$, 19.7°, 26.5° and 29.0°, and its X-ray diffraction pattern was close to that of a partial strontium salt substitution product of molybdovanadophosphoric acid.

The catalyst showed good moldability and had a compression strength of more than 3.0 kg/pellet. The same reaction as in Example 5 was carried out using this catalyst, and the results are shown in Table 3.

Comparative Example 4

A catalyst having the same composition as in Example 6 was obtained in the same way as in Example 6 except that pyridine was not used, and the step of removing pyridine by calcination in a stream of nitrogen at 430° C. for 3 hours was omitted. The X-ray diffraction analsysis of the catalyst showed that main diffraction lines appeared at $2\theta=8.9°$, 19.7°, 26.7° and 29.0°. This catalyst was hydroscopic and very fragile. The same reaction as in Example 6 was carried out using the resulting catalyst, and the results are shown in Table 4.

EXAMPLE 7

A catalytic oxide having the composition P:Mo:V:Cs=1.09:12:1.09:1 (atomic ratio excepting oxygen) was prepared in the same way as in the same way as in Example 5 (method C) except that piperidine was used instead of pyridine and the amount of cesium nitrate was changed to 8.12 g. The X-ray diffraction analysis of the catalyst showed that main diffraction lines appeared at $2\theta=26.3°$, 10.6°, 21.4°, 30.4° and 18.4°. The catalyst had a compression strength of more than 3.0 kg/pellet. The same reaction as in Example 5 was carried out using the resulting catalyst, and the results are shown in Table 3.

EXAMPLE 8

A catalytic oxide having the composition P:Mo:V:Sr=1.09:12:1.09:0.6 (atomic ratio excepting oxygen) was prepared in the same way as in Example 6 (method C) excepting that 12 g of piperazine hexahydrate was used instead of pyridine and the amount of strontium nitrate was changed to 5.29 g. The X-ray diffraction analysis of the catalyst showed that its X-ray diffraction pattern was quite identical with that of the catalyst obtained in Example 6. The catalyst had a compression strength of more than 3.0 kg/pellet. The same reaction as in Example 5 was carried out using the resulting catalyst, and the results are shown in Table 3.

EXAMPLE 9

Ammonium paramolybdate (88.3 g) and 5.36 g of ammonium metavanadate were dissolved in 200 ml of hot water, and the solution was stirred. To the solution were added 20 g of pyridine and 5.28 g of phosphoric acid (85% by weight), followed by addition of 40 ml of nitric acid to give orange yellow crystals. The crystals were collected by filtration and dispersed in 100 ml of water. A solution of 5.12 g of rubidium hydroxide in 50 ml of water was added to the dispersion, and with stirring, the mixture was concentrated by heating. The resulting clay-like material was molded into cylindrical pellets having a diameter of 5 mm and a height of 5 mm, dried at 250° C., calcined in a stream of nitrogen at 450° C. for 4 hours, and then calcined in a stream of air at 400° C. for 2 hours to give a catalytic oxide having the composition P:Mo:V:Rb=1.1:12:1.1:1.2 (atomic ratio excepting oxygen) (this method of preparation is referred to hereinbelow as method D).

The catalyst had a compression strength of more than 3.0 kg/pellets. The same reaction as in Example 1 was carried out continuously except that the reaction temperature was changed to 290° C., and the results are shown in Table 3.

EXAMPLE 10

A catalyst having the composition P:Mo:V:Rb=1.1:12:1.1:12 (atomic ratio excepting oxygen) was prepared in the same way as in Example 9 (method D) except that 7.0 g of ammonium nitrate was further added in the step of adding the aqueous solution of rubidium hydroxide. The same reaction as in Example 9 was carried out using this catalyst, and the results are shown in Table 3.

EXAMPLE 11

A catalytic oxide having the composition P:Mo:V:Be:Ba=1.1:12:1.1:0.3:0.8 (atomic ratio excepting oxygen) was prepared in the same way as in Example 9 (method D) except that 2.34 g of beryllium nitrate and 8.71 g of barium nitrate were used instead of rubidium hydroxide. The same reaction as in Example 1 was carried out using this catalyst except that the reaction temperature was changed to 280° C. The results are shown in Table 3.

EXAMPLE 12

Ammonium paramolybdate (88.3 g) and 4.87 g of ammonium metavanadate were dissolved in 200 ml of hot water, and the solution was stirred. To the solution was added 20 g of pyridine and 6.25 g of phosphoric acid (85% by weight), and subsequently, 40 ml of nitric acid and a solution of 8.12 g of cesium nitrate in 50 ml of water were added. With stirring, the mixture was concentrated by heating. The resulting clay-like material was molded into cylindrical pellets having a diameter of 5 mm and a height of 5 mm, dried at 250° C., calcined in a stream of nitrogen at 450° C. for 4 hours, and then calcined in a stream of air at 400° C. for 2 hours to give a catalytic oxide having the composition P:Mo:V:Cs=1.3:12:1:1 (atomic ratio excepting oxygen) (this method of preparation is referred to hereinbelow as method B'). The X-ray diffraction analysis of the catalyst showed that main diffraction lines appeared at $2\theta=26.2°, 10.5°, 21.3°, 30.3°$ and $18.4°$. The catalyst had a compression strength of more than 3.0 kg/pellet. The same reaction as in Example 1 was carried out using the resulting catalyst except that the reaction temperature was changed to 280° C. The results are shown in Table 3.

Comparative Example 5

A catalytic oxide having the same composition as in Example 12 was prepared in the same way as in Example 12 except that pyridine was not used. The catalyst showed poor moldability, and had a compression strength of less than 0.5 kg/pellet. The same reaction as in Example 12 was carried out using this catalyst, and the results are shown in Table 4.

EXAMPLES 13 TO 20

In each run, a catalyst having each of the compositions shown in Table 3 was prepared in the same way as in Example 12 except that pyridine or piperidine was used as the nitrogen-containing heterocyclic compound, the amounts of ammonium metavanadate and phosphoric acid used were changed, and at least one compound selected from sodium nitrate, potassium nitrate, rubidium hydroxide, thallium nitrate, magnesium nitrate, calcium nitrate, strontium nitrate and barium nitrate was used as the component X (method B'). The same reaction as in Example 1 was carried out using the resulting catalyst. The results are shown in Table 3.

EXAMPLE 21

A catalytic oxide having the composition P:Mo:V:Te=1.09:12:1.09:0.2 (atomic ratio excepting oxygen) was prepared in the same way as in Example 5 (method C) except that 1.91 g of telluric acid was used instead of cesium nitrate. The same reaction as in Example 1 was carried out in the same way as in Example 1 except that the reaction temperature was changed to 290° C. The results are shown in Table 5.

EXAMPLE 22

A catalytic oxide having the composition P:Mo:V:Rb:Cu=1.09:12:1.09:0.1:0.1 (atomic ratio excepting oxygen) was prepared in the same way as in Example 5 (method C) except that 0.43 g of rubidium hydroxide and 1.0 g of copper nitrate were used instead of cesium nitrate.

The X-ray diffraction analysis of the catalyst showed that main diffraction lines appeared at $2\theta=26.3°, 10.6°, 21.3°, 30.5°$ and $18.5°$. The catalyst showed good moldability and had a compression strength of more than 3.0 kg/pellet.

The same reaction as in Example 1 was carried out except that the reaction temperature was changed to 270° C. The results are shown in Table 5.

Comparative Example 6

A catalyst having the same composition as in Example 22 and not treated with pyridine was prepared in the same way as in Example 5 except as noted below. 81.0 g of the resulting molybdovanadophosphoric acid were dissolved in 200 ml of water, and a solution of 0.43 g of rubidium hydroxide and 1.0 g of copper nitrate in 20 ml of water was added to the aqueous solution, the mixture was concentrated by heating. The residue was molded into cylindrical pellets having a diameter of 5 mm and a height of 5 mm, dried and then calcined in a stream of air at 400° C. for 3 hours. The X-ray diffraction analysis of the resulting catalyst showed that main diffraction lines appeared at $2\theta = 8.9°$, 26.4°, 19.7°, 30.6°, and 18.6°, and in particular, the diffraction line assgined to free molybdovanadophosphoric acid ($2\theta = 8.9°$) had a relatively high intensity. The catalyst was very fragile and had a compression strength of less than 0.5 kg/pellet. The same reaction as in Example 22 was carried out using this catalyst. The results are shown in Table 6.

EXAMPLE 23

A catalyst having the same composition as in Example 22 was obtained in the same way as in Example 22 except that 7.0 g of ammonium nitrate was simultaneously added in the step of adding rubidium hydroxide and copper nitrate (method C). The same reaction as in Example 22 was carried out using this catalyst, and the results are shown in Table 6.

EXAMPLE 24

A catalytic oxide having the composition P:Mo:V:Sr:Cu=1.09:12:1.09:0.1:0.1 (atomic ratio excepting oxygen) was prepared in the same way as in Example 22 (method C) except that 0.88 g of strontium nitrate was used instead of rubidium hydroxide. The X-ray diffraction analysis of the catalyst showed that main diffraction lines appeared at $2\theta = 26.1°$, 10.5°, 21.3°, and 30.3°. A part of the catalyst was dispersed in water, and the dispersion was evaporated to dryness. The residue was calcined and subjected to X-ray diffraction analysis. It was found that main diffraction lines appeared at $2\theta = 8.9°$, 19.7°, 26.5° and 29.0°.

The same reaction as in Example 1 was carried out except that the reaction temperature was changed to 260° C. The results are shown in Table 5.

Comparative Example 7

A catalyst having the same composition as in Example 24 was prepared in the same way as in Example 24 except that pyridine was not used, and the step of removing pyridine by calcination at 430° C. for 3 hours in a stream of nitrogen was omitted. X-ray diffraction analysis showed that main diffraction lines appeared at $2\theta = 8.9°$, 19.7°, 26.7° and 29.0°. The resulting catalyst was hygroscopic and very fragile. The same reaction as in Example 24 was carried out using this catalyst. The results are shown in Table 6.

EXAMPLES 25 AND 26

Catalysts having the compositions shown in Table 5 were obtained in the same way as in Example 22 (method C) except that piperidine or piperazine hexahydrate was used instead of pyridine. The same reaction as in Example 1 was carried out using each of these catalysts at each of the reaction temperatures shown in Table 5. The results are shown in Table 5.

EXAMPLE 27

A catalytic oxide having the composition P:Mo:V:Cs:Ag=1.3:12:1:1:0.1 (atomic ratio excepting oxygen) was prepared in the same way as in Example 12 (method B') except that 0.71 g of silver nitrate was added as component Y in the step of adding cesium nitrate. The same reaction as in Example 12 was carried out using the resulting catalyst. The results are shown in Table 5.

Comparative Example 8

A catalytic oxide having the same composition as in Example 27 was obtained in the same way as in Example 27 except that pyridine was not used. The same reaction as in Example 27 was carried out using the resulting catalyst. The results are shown in Table 6.

EXAMPLES 28 TO 41

Catalysts having the compositions shown in Table 5 were prepared in accordance with the method of Example 27 (method B') by using pyridine as the nitrogen-containing heterocyclic compound, varying amounts of ammonium metavanadate and phosphoric acid, at least one compound as component X selected from rubidium hydroxide and the nitrates of sodium, potassium, cesium, thallium, beryllium, magnesium, calcium, strontium and barium and at least one compound as component Y selected from copper nitrate, silver nitrate, ortho-arsenic acid, antimony trioxide, telluric acid, cobalt nitrate, bismuth nitrate and zirconium nitrate. The same reaction as in Example 1 was carried out using each of these catalysts. The results are shown in Table 5.

EXAMPLE 42

A catalytic oxide having the composition P:Mo:V:Cs=1.3:12:1:0.5 (atomic ratio excepting oxygen) was prepared in the same way as in Example 12 (method B') except that the amount of cesium nitrate was changed to 4.06 g. The same reaction as in Example 1 was carried out using the resulting catalyst except that isobutyraldehyde was used instead of methacrolein and the reaction temperature was changed to 270° C. After the lapse of 100 hours, the results shown in Table 7 were obtained. The one-pass yield of methacrolein in the table is the mole percent of the resulting methacrolein based on the fed isobutyraldehyde.

Comparative Example 9

A catalyst having the same composition as in Example 42 was prepared in the same way as in Example 42 except that pyridine was not used. The same reaction as in Example 42 was carried out using the resulting catalyst. The results are shown in Table 8.

EXAMPLE 43

Using the catalyst prepared in Example 13 (method B') isobutyraldehyde was oxidized in the same way as in Example 42. The results are shown in Table 7.

Comparative Example 10

A catalyst having the same composition as in Example 13 was prepared in the same way as in Example 13 except that pyridine was not used. The same reaction as in Example 42 was carried out using this catalyst. The results are shown in Table 8.

EXAMPLE 44

A catalytic oxide having the composition P:Mo:V:Cs:Ag=1.3:12:1:0.5:0.1 (atomic ratio excepting oxygen) was prepared in the same way as in Example 27 (method B') except that the amount of cesium nitrate was changed to 4.06 g. Using the resulting catalyst, isobutyraldehyde was oxidized in the same way as in Example 42. The results are shown in Table 7.

Comparative Example 11

A catalyst having the same composition as in Example 44 was prepared in the same way as in Example 44 except that pyridine was not used. The same reaction as in Example 42 was carried out using the resulting catalyst. The results are shown in Table 8.

EXAMPLE 45

Using the catalyst prepared in Example 28 (method B'), isobutyraldehyde was oxidized in the same way as in Example 42. The results are shown in Table 7.

Comparative Example 12

A catalyst having the same composition as in Example 28 was prepared in the same way as in Example 28 except that pyridine was not used. The same reaction as in Example 42 was carried out using the resulting catalyst. The results are shown in Table 8.

TABLE 1

| Example | Method of preparation | Nitrogen-containing heterocyclic compound | Reaction temperature (°C.) | Conversion of methacrolein (%) | Selectivity for methacrylic acid (%) | One-pass yield of methacrylic acid (%) |
|---|---|---|---|---|---|---|
| 1 | A | Pyridine | 290 | 92.7 | 82.9 | 76.8 |
| 2 | A | Piperidine | 280 | 89.2 | 76.7 | 68.4 |
| 3 | A | Piperazine | 300 | 95.6 | 75.2 | 71.9 |
| 4 | B | Pyridine | 300 | 94.5 | 84.6 | 79.9 |

TABLE 2

| Comparative Example | Nitrogen containing heterocyclic compound | Reaction temperature (°C.) | Conversion of methacrolein (%) | Selectivity for methacrylic acid (%) | One-pass yield of methacrylic acid % |
|---|---|---|---|---|---|
| 1 | None | 290 | 73.7 | 54.7 | 40.3 |
| 2 | None | 300 | 71.8 | 62.1 | 44.6 |

TABLE 3

| Example | Method of preparation | Nitrogen-containing heterocyclic compound | Composition of the catalyst (atomic ratio excepting oxygen) P | Mo | V | X | Reaction temperature (°C.) | Reaction time elapsed (hr) | Conversion of methacrolein (%) | Selectivity for methacrylic acid (%) | One-pass yield of methacrylic acid (%) |
|---|---|---|---|---|---|---|---|---|---|---|---|
| 5 | C | Pyridine | 1.09 | 12 | 1.09 | Cs = 0.1 | 260 | 100 | 92.9 | 85.7 | 79.6 |
|   |   |   |   |   |   |   |   | 1000 | 91.5 | 85.8 | 78.5 |
| 6 | C | Pyridine | 1.09 | 12 | 1.09 | Sr = 0.1 | 260 | 100 | 93.7 | 84.0 | 78.7 |
|   |   |   |   |   |   |   |   | 1000 | 92.9 | 84.1 | 78.1 |
| 7 | C | Piperidine | 1.09 | 12 | 1.09 | Cs = 1 | 260 | 100 | 92.6 | 84.2 | 78.0 |
|   |   |   |   |   |   |   |   | 1000 | 91.8 | 85.1 | 78.1 |
| 8 | C | Piperazine | 1.09 | 12 | 1.09 | Sr = 0.6 | 260 | 100 | 91.6 | 83.7 | 76.7 |
|   |   |   |   |   |   |   |   | 1000 | 90.0 | 83.9 | 75.5 |
| 9 | D | Pyridine | 1.1 | 12 | 1.1 | Rb = 1.2 | 290 | 100 | 93.5 | 84.6 | 79.1 |
|   |   |   |   |   |   |   |   | 1000 | 92.6 | 84.9 | 78.6 |
| 10 | D | Pyridine | 1.1 | 12 | 1.1 | Rb = 1.2 | 290 | 100 | 92.2 | 86.8 | 80.0 |
| 11 | D | Pyridine | 1.1 | 12 | 1.1 | Be = 0.3 Ba = 0.8 | 280 | 100 | 92.5 | 86.3 | 79.8 |
|   |   |   |   |   |   |   |   | 1000 | 92.0 | 86.7 | 79.8 |
| 12 | B' | Pyridine | 1.3 | 12 | 1 | Cs = 1 | 280 | 100 | 93.8 | 86.4 | 81.0 |
|   |   |   |   |   |   |   |   | 1000 | 92.9 | 86.6 | 80.5 |
| 13 | B' | Pyridine | 1.3 | 12 | 1 | Ba = 1 | 270 | 100 | 91.8 | 85.7 | 78.7 |
|   |   |   |   |   |   |   |   | 1000 | 90.4 | 86.1 | 77.8 |
| 14 | B' | Piperidine | 1.5 | 12 | 2 | K = 1.5 | 270 | 100 | 94.6 | 84.1 | 79.6 |
| 15 | B' | Pyridine | 1.3 | 12 | 2 | Mg = 1 | 270 | 100 | 92.7 | 86.0 | 79.7 |
| 16 | B' | Pyridine | 1.1 | 12 | 0.5 | Rb = 0.5 Tl = 0.7 | 290 | 100 | 92.8 | 87.3 | 81.0 |
| 17 | B' | Pyridine | 1.3 | 12 | 2 | Na = 0.5 Rb = 1.5 | 280 | 100 | 95.1 | 84.4 | 80.3 |
| 18 | B' | Piperidine | 1.3 | 12 | 1 | K = 1 Sr = 0.4 | 260 | 100 | 93.3 | 86.2 | 80.4 |
| 19 | B' | Piperidine | 1.3 | 12 | 1.5 | Sr = 0.5 Ca = 0.8 | 260 | 100 | 93.3 | 85.8 | 80.1 |
| 20 | B' | Pyridine | 1.2 | 12 | 1.8 | Sr = 0.8 Ba = 1 | 260 | 100 | 92.1 | 87.0 | 80.1 |

TABLE 4

| Comparative Example | Nitrogen-containing heterocyclic compound | Composition of the catalyst (atomic ratio excepting oxygen) | | | | Reaction temperature (°C.) | Reaction time elapsed (hr.) | Conversion of methacrolein (%) | Selectivity for methacrylic acid (%) | One-pass yield of methacrylic acid (%) |
|---|---|---|---|---|---|---|---|---|---|---|
| | | P | Mo | V | X | | | | | |
| 3 | None | 1.09 | 12 | 1.09 | Cs = 0.1 | 260 | 100 | 78.6 | 75.4 | 59.3 |
| | | | | | | | 1000 | 72.5 | 70.8 | 51.3 |
| 4 | None | 1.09 | 12 | 1.09 | Sr = 0.1 | 260 | 100 | 72.4 | 64.3 | 46.6 |
| | | | | | | | 1000 | 67.5 | 62.8 | 42.4 |
| 5 | None | 1.3 | 12 | 1 | Cs = 1 | 280 | 100 | 86.4 | 73.9 | 63.8 |
| | | | | | | | 1000 | 81.3 | 69.7 | 56.7 |

TABLE 5

| Example | Method of preparation | Nitrogen-containing heterocyclic compound | Composition of the catalyst (atomic ratio excepting oxygen) | | | | | Reaction temperature (°C.) | Reaction time elapsed (hr.) | Conversion of methacrolein (%) | Selectivity for methacrylic acid (%) | One-pass yield of methacrylic acid (%) |
|---|---|---|---|---|---|---|---|---|---|---|---|---|
| | | | P | Mo | V | X | Y | | | | | |
| 21 | C | Pyridine | 1.09 | 12 | 1.09 | — | Te = 0.2 | 290 | 100 | 93.6 | 84.9 | 79.5 |
| 22 | C | Pyridine | 1.09 | 12 | 1.09 | Rb = 0.1 | Cu = 0.1 | 270 | 100 | 93.4 | 86.5 | 80.8 |
| | | | | | | | | | 1000 | 92.5 | 86.6 | 80.1 |
| 23 | C | Pyridine | 1.09 | 12 | 1.09 | Rb = 0.1 | Cu = 0.1 | 270 | 100 | 93.6 | 87.4 | 81.8 |
| | | | | | | | | | 1000 | 92.1 | 87.9 | 81.0 |
| 24 | C | Pyridine | 1.09 | 12 | 1.09 | Sr = 0.1 | Cu = 0.1 | 260 | 100 | 92.6 | 86.4 | 80.0 |
| | | | | | | | | | 1000 | 92.0 | 86.7 | 79.8 |
| 25 | C | Piperidine | 1.09 | 12 | 1.09 | Rb = 1 | Cu = 0.1 | 270 | 100 | 92.9 | 85.1 | 79.1 |
| | | | | | | | | | 1000 | 91.7 | 85.6 | 78.5 |
| 26 | C | Piperazine | 1.09 | 12 | 1.09 | Sr = 0.6 | Cu = 0.1 | 260 | 100 | 92.3 | 85.5 | 78.9 |
| | | | | | | | | | 1000 | 91.1 | 85.9 | 78.3 |
| 27 | B' | Pyridine | 1.3 | 12 | 1 | Cs = 1 | Ag = 0.1 | 280 | 100 | 92.7 | 88.3 | 81.9 |
| | | | | | | | | | 1000 | 92.1 | 88.6 | 81.6 |
| 28 | B' | Pyridine | 1.3 | 12 | 1 | Ba = 1 | Ag = 0.1 | 270 | 100 | 93.3 | 87.4 | 81.5 |
| | | | | | | | | | 1000 | 92.1 | 88.0 | 81.0 |
| 29 | B' | Pyridine | 1.5 | 12 | 2 | K = 1.5 | Ag = 0.1 | 270 | 100 | 93.6 | 86.2 | 80.7 |
| 30 | B' | Pyridine | 1.1 | 12 | 0.5 | Rb = 0.5 Tl = 0.7 | Cu = 0.1 | 290 | 100 | 92.0 | 88.5 | 81.4 |
| 31 | B' | Pyridine | 1.3 | 12 | 2 | Na = 0.5 Rb = 1.5 | Cu = 0.1 | 280 | 100 | 93.5 | 87.0 | 81.3 |
| 32 | B' | Pyridine | 1.3 | 12 | 1 | Cs = 1 | Ag = 0.1 As = 0.3 | 270 | 100 | 92.4 | 88.7 | 82.0 |
| 33 | B' | Pyridine | 1.5 | 12 | 1 | Rb = 1 | Te = 0.25 | 280 | 100 | 92.3 | 87.7 | 80.9 |
| 34 | B' | Pyridine | 1.3 | 12 | 1 | Cs = 1 | Co = 0.2 Sb = 1.5 | 270 | 100 | 92.8 | 87.9 | 81.6 |
| 35 | B' | Pyridine | 1.3 | 12 | 1 | Cs = 1 | Cu = 0.2 Bi = 1 | 270 | 100 | 92.6 | 88.4 | 81.9 |
| 36 | B' | Pyridine | 1.3 | 12 | 1 | Cs = 1 | Cu = 0.1 Zr = 0.5 | 280 | 100 | 93.3 | 88.0 | 82.1 |
| 37 | B' | Pyridine | 1.3 | 12 | 1 | Cs = 1 Sr = 0.2 | Ag = 0.1 | 280 | 100 | 92.5 | 88.6 | 82.0 |
| 38 | B' | Pyridine | 1.1 | 12 | 1.1 | Be = 0.3 Ba = 0.8 | Ag = 0.1 | 280 | 100 | 92.5 | 87.6 | 81.0 |
| 39 | B' | Pyridine | 1.3 | 12 | 2 | Sr = 1.0 Ca = 1.5 | Cu = 0.2 | 250 | 100 | 91.7 | 88.1 | 80.8 |
| 40 | B' | Pyridine | 1.3 | 12 | 2 | Mg = 1 | Co = 0.3 Sb = 1.5 | 260 | 100 | 93.6 | 86.3 | 80.8 |
| 41 | B' | Pyridine | 1.3 | 12 | 1 | Sr = 0.6 | Cu = 0.1 As = 0.3 | 270 | 100 | 92.9 | 88.3 | 82.0 |

TABLE 6

| Comparative Example | Nitrogen-containing heterocyclic compound | Composition of the catalyst (atomic ratio excepting oxygen) | | | | | Reaction temperature (°C.) | Reaction time elapsed (hr.) | Conversion of methacrolein (%) | Selectivity for methacrylic acid (%) | One-pass yield of methacrylic acid (%) |
|---|---|---|---|---|---|---|---|---|---|---|---|
| | | P | Mo | V | X | Y | | | | | |
| 6 | None | 1.09 | 12 | 1.09 | Rb = 0.1 | Cu = 0.1 | 270 | 100 | 86.2 | 73.5 | 63.4 |
| | | | | | | | | 1000 | 81.4 | 69.3 | 56.4 |
| 7 | None | 1.09 | 12 | 1.09 | Sr = 0.1 | Cu = 0.1 | 260 | 100 | 81.3 | 60.7 | 49.3 |
| | | | | | | | | 1000 | 72.4 | 58.3 | 42.2 |
| 8 | None | 1.3 | 12 | 1 | Cs = 1 | Ag = 0.1 | 280 | 100 | 90.3 | 74.5 | 67.3 |

TABLE 6-continued

| Comparative Example | Nitrogen-containing heterocyclic compound | Composition of the catalyst (atomic ratio excepting oxygen) | | | | | Reaction temperature (°C.) | Reaction time elapsed (hr.) | Conversion of methacrolein (%) | Selectivity for methacrylic acid (%) | One-pass yield of methacrylic acid (%) |
|---|---|---|---|---|---|---|---|---|---|---|---|
| | | P | Mo | V | X | Y | | | | | |
| | | | | | | | | 1000 | 83.7 | 72.0 | 60.3 |

TABLE 7

| Example | Composition of the catalyst (atomic ratio excepting oxygen) | | | | | Reaction temperature (°C.) | Conversion of isobutyraldehyde (%) | One-pass yield of methacrylic acid (%) | One-pass yield of methacrolein (%) |
|---|---|---|---|---|---|---|---|---|---|
| | P | Mo | V | X | Y | | | | |
| 42 | 1.3 | 12 | 1 | Cs = 0.5 | — | 270 | 100 | 65.7 | 11.4 |
| 43 | 1.3 | 12 | 1 | Ba = 1 | — | 280 | 100 | 64.6 | 10.2 |
| 44 | 1.3 | 12 | 1 | Cs = 0.5 | Ag = 0.1 | 280 | 100 | 69.3 | 9.2 |
| 45 | 1.3 | 12 | 1 | Ba = 1 | Ag = 0.1 | 280 | 100 | 68.1 | 8.5 |

TABLE 8

| Comparative Example | Nitrogen-containing heterocyclic compound | Composition of the catalyst (atomic ratio excepting oxygen) | | | | | Reaction temperature (°C.) | Conversion of isobutyraldehyde (%) | One-pass yield of methacrylic acid (%) | One-pass yield of methacrolein (%) |
|---|---|---|---|---|---|---|---|---|---|---|
| | compound | P | Mo | V | X | Y | | | | |
| 9 | None | 1.3 | 12 | 1 | Cs = 0.5 | — | 270 | 100 | 43.9 | 12.7 |
| 10 | None | 1.3 | 12 | 1 | Ba = 1 | — | 280 | 100 | 39.0 | 15.9 |
| 11 | None | 1.3 | 12 | 1 | Cs = 0.5 | Ag = 0.1 | 280 | 100 | 44.5 | 11.3 |
| 12 | None | 1.3 | 12 | 1 | Ba = 1 | Ag = 0.1 | 280 | 100 | 39.4 | 13.8 |

What we claim is:

1. A catalyst for the vapor-phase oxidation of an unsaturated hydrocarbon, alcohol, saturated aliphatic aldehyde or unsaturated aliphatic aldehyde having 4 carbon atoms, said catalyst comprising molybdovanadophosphoric acid and being formed by adding a nitrogen-containing heterocyclic compound selected from the group consisting of pyridine, piperidine and piperazine to an aqueous solution of molybdovanadophosphoric acid to form a precipitate, pelletizing, drying and calcining and has X-ray diffraction lines (Cu-K$_\alpha$radiation) at $2\theta=$ about 26.2°, about 10.5°, about 21.3° and about 30.3° and a crystal structure approximating that of its salt, and said catalyst having the composition represented by the general formula $$P_a Mo_b V_c X_d Y_e O_f$$

wherein the dissociable protons of the molybdovanadophosphoric acid are omitted, X represents at least one element selected from the group consisting of sodium, potassium, rubidium, cesium, thallium, beryllium, magnesium, calcium, strontium, and barium, Y represents at least one element selected from the group consisting of copper, silver, arsenic, antimony, tellurium, cobalt, bismuth and zirconium, and the subscripts a to f represent the atomic proportions of the respective elements, provided that when b is 12, a is 0.1–3.0,
c is 0.1–6.0
d is 0–10.0
e is 0–5.0, and
f is a value determined by the atomic valences and atomic proportions of the respective elements.

2. The catalyst of claim 1 wherein the subscripts a to f represent the following numbers: b is 12, a is 0.1–2.0,
c is 0.1–4.0,
d is 0–5.0, and
e is 0–5.0.